United States Patent
Yakhno et al.

(10) Patent No.: US 7,350,402 B2
(45) Date of Patent: *Apr. 1, 2008

(54) METHOD AND APPARATUS FOR DETERMINATION OF MEDICAL DIAGNOSTICS UTILIZING BIOLOGICAL FLUIDS

(75) Inventors: Tatjana Anatoljevna Yakhno, Nizhny Novgorod (RU); Anatoly Gennadievich Sanin, Nizhny Novgorod (RU); Vladimir Grigorievich Yakhno, Nizhny Novgorod (RU); Artem S. Pelushenko, Nizhny Novgorod (RU); Michael B. Dowell, Hudson, OH (US); Christina V. Vacca, Avon, OH (US); Valentina B. Goutorova, Twinsburg, OH (US)

(73) Assignee: Aria Analytics, Inc., Cleveland, OH (US)

( * ) Notice: Subject to any disclaimer, the term of this patent is extended or adjusted under 35 U.S.C. 154(b) by 264 days.

This patent is subject to a terminal disclaimer.

(21) Appl. No.: 11/098,219

(22) Filed: Apr. 4, 2005

(65) Prior Publication Data
US 2005/0262926 A1    Dec. 1, 2005

Related U.S. Application Data

(63) Continuation-in-part of application No. 10/466,845, filed on Jul. 21, 2003, now Pat. No. 6,874,357.

(51) Int. Cl.
*G01N 29/00*    (2006.01)

(52) U.S. Cl. .................. 73/64.53; 73/53.04; 73/61.73; 73/574

(58) Field of Classification Search .................. 73/649, 73/64.53, 53.04, 61.73, 574, 54.07, 61.74, 73/54.24, 24.01, 335.03, 335.06, 61.45, 61.77, 73/61.79
See application file for complete search history.

(56) References Cited

U.S. PATENT DOCUMENTS 2,876,083 A * 3/1959 Prietl ........................ 23/295 R (Continued)

OTHER PUBLICATIONS

Angel Rodriguez-Vazquez et al. A Method for Liquid Analysis by Means of Recording the Dynamics of Phase Tranistions During Drop Drying May 19-21, 2003.

(Continued)

*Primary Examiner*—Hezron Williams
*Assistant Examiner*—Jacques M. Saint-Surin

(57) ABSTRACT

A method for measuring changes in the composition of fluids, for medical diagnostics or quality control of fluids, comprising:
  One) placing a drop of fluid upon a quartz crystal;
  Two) generating ultrasonic vibrations of a predetermined frequency in the crystal; with the vibrating wave directed into the drop of fluid in a vertical direction relative to the area of the crystal upon which the drop is placed;
  Three) measuring voltage changes over a bridge circuit connected to the crystal, over a time period during which total or partial evaporation of the liquid occurs;
  Four) comparing the measurement result to previously obtained results or to predetermined data;
  Five) detecting changes in the composition of the fluid, from the results. detecting changes in the composition of the fluid, from said results.

17 Claims, 5 Drawing Sheets

Differences in the dynamics of phase transitions during drying of plasma drops in women with normal pregnancy and in the case of threatened abortion (premature childbirth).

U.S. PATENT DOCUMENTS

| | | | | |
|---|---|---|---|---|
| 5,706,815 A | * | 1/1998 | Sarvazyan et al. | 600/438 |
| 5,798,452 A | * | 8/1998 | Martin et al. | 73/32 R |
| 6,141,625 A | * | 10/2000 | Smith et al. | 702/50 |
| 6,393,895 B1 | * | 5/2002 | Matsiev et al. | 73/24.06 |
| 6,401,519 B1 | * | 6/2002 | McFarland et al. | 73/24.06 |
| 6,494,079 B1 | * | 12/2002 | Matsiev et al. | 73/24.05 |
| 6,725,707 B1 | * | 4/2004 | Lin et al. | 73/54.01 |
| 6,854,338 B2 | * | 2/2005 | Khuri-Yakub et al. | 73/861.27 |
| 6,874,357 B2 | * | 4/2005 | Yakhno et al. | 73/64.53 |
| 6,904,786 B2 | * | 6/2005 | Matsiev et al. | 73/24.06 |
| 6,957,565 B2 | * | 10/2005 | Matsiev et al. | 73/24.06 |
| 7,043,969 B2 | * | 5/2006 | Matsiev et al. | 73/54.41 |
| 7,073,370 B2 | * | 7/2006 | Matsiev et al. | 73/24.06 |
| 2007/0241756 A1 | * | 10/2007 | Mizukami et al. | 324/444 |

OTHER PUBLICATIONS

T. A. Yakhno et al. Study of the Dynamics of Phase Transitions in Liquids of Different Types by Measuring the Acoustomechanical Impedance of a Drying Drop Jul. 17, 2002.

T. A. Yakhno, et al. New Universal Electronic Tongue & Nose and Its Possibilities in Food Examinations Sep. 24-26, 2003.

T. A. Yakhno et al. On the Existence of Regular Structures in Liquid Human Blood Serum (Plasma) and Phase Transitions in the Course of Its Drying Sep. 3, 2002.

T. A. Yakhno et al. The Informative-Capacity Phenomenon of Drying Drops. Aptitude Test in Medical Diagnostics 2004.

T. A. Yakhno et al. Drying Drops of Biological Liquids: Dynamics of the Optical and Mechanical Properties. Application in Rapid Medical Diagnostics Dec. 22, 2004.

T. Yakhno et al. Dynamics of Phase Transitions in Drying Drops as an Information Parameter of Liquid Structure Jul. 2004.

* cited by examiner

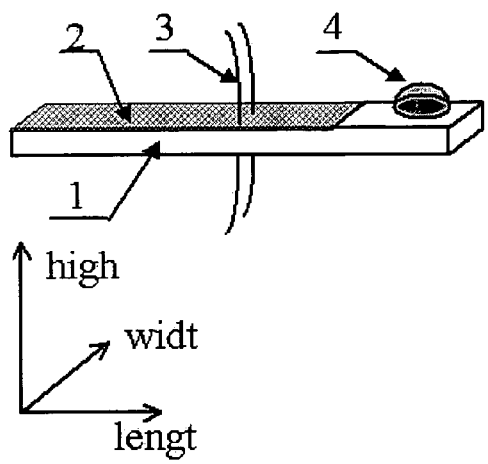
Fig.1. Quartz resonator with a drop of studied liquid: 1 is a quartz plate, 2 is the metallization, 3 is the supporting conductors, 4 is a drop of studied liquid.
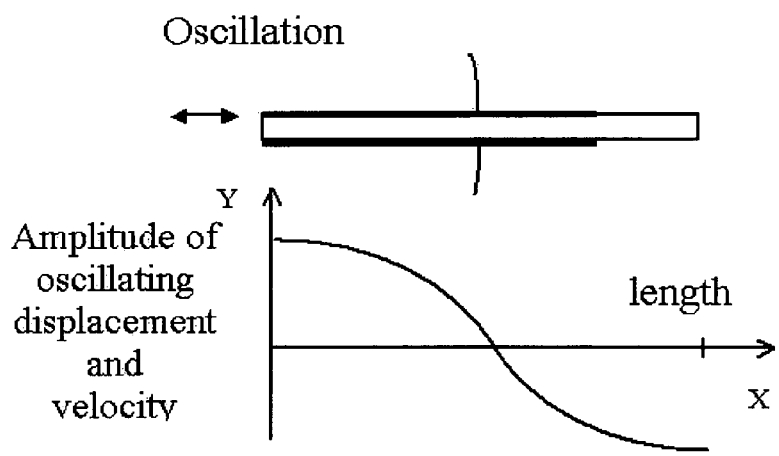
Fig. 2. Distribution of the oscillatory velocity amplitude and longitudinal displacement of the quartz plate.

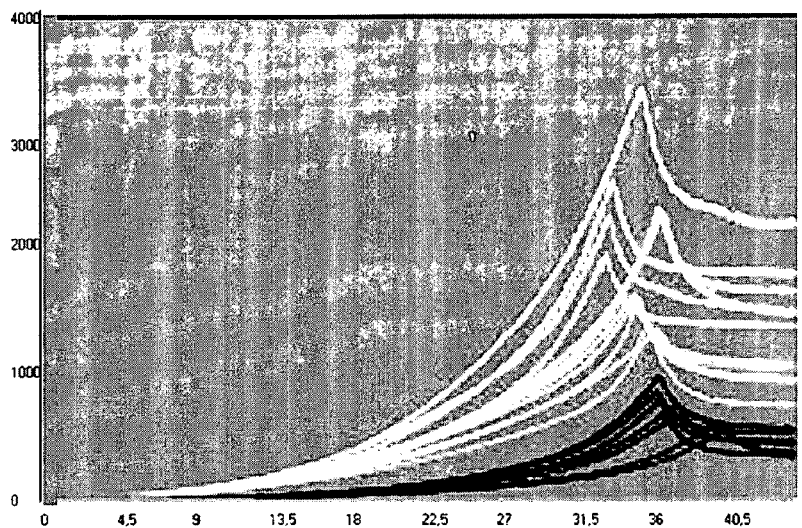

Fig. 3. Specific features of unprocessed experimental AMI curves of drying drops of serum from women after premature (II trimester) childbirths (black) against in-time childbirth (white).
X - axis is the time (min), Y - axis is the AMI (recorded units).

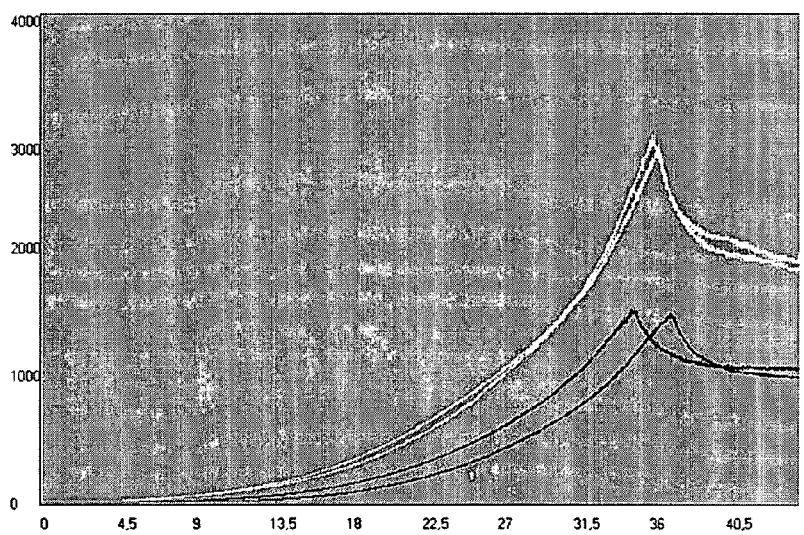

Fig.4. Specific features of unprocessed experimental AMI curves of drying drops of serum from woman of 34-weeks of gestation with threaten abortion (black, two curves for one sample) against 34-weeks normal pregnancy (white, two curves for one sample).
X - axis is the time (min), Y - axis is the AMI (recorded units).

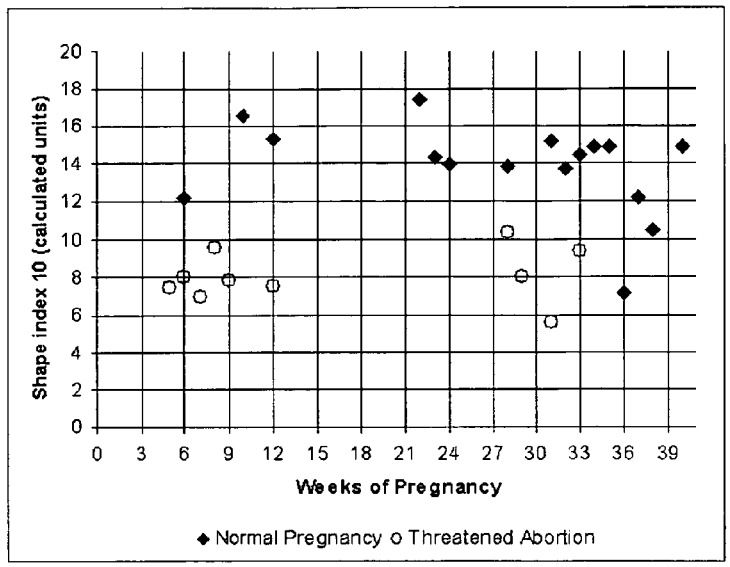

Fig. 5. Differences in the dynamics of phase transitions during drying of plasma drops in women with normal pregnancy and in the case of threatened abortion (premature childbirth).

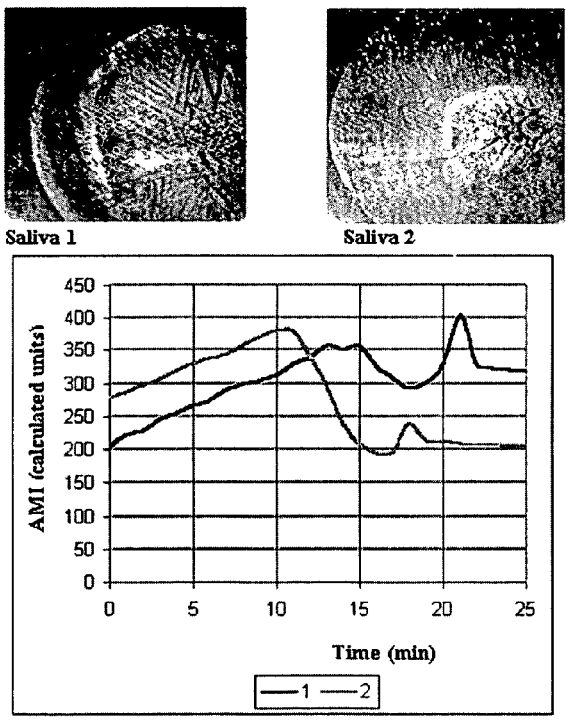

Fig. 6. Dried drops of saliva of two donors, and dynamics of the AMI during their drying: different proportion between protein zone (periphery) and salt zone (centre) is traced by the AMI signal.

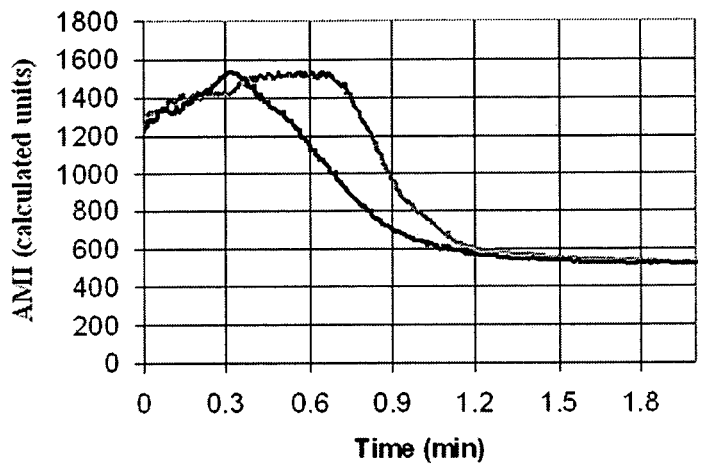

Fig. 7. Dynamics of the AMI of drying drops of two kinds of gasoline with different Octane Number: A-76 (black) and A-92 (white).
The X axis is the time (min) and the Y axis is the AMI (calculated units).

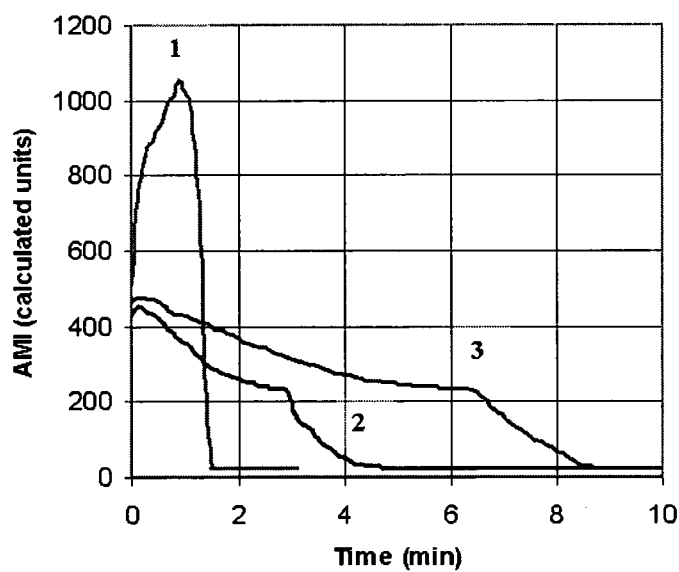

Fig. 8. Dynamics of the AMI of the drying drops of ethyl spirit (1), vodka "Nizhegorodsky Gubernator"(2), and Scotch whisky "Chivas regal – premium" (3).
The X axis is the time (min) and the Y axis is the AMI (calculated units).

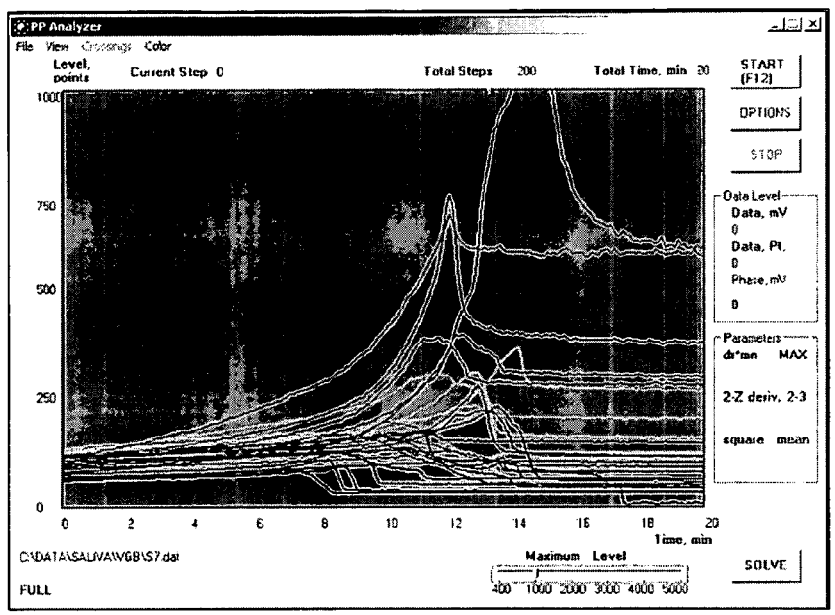
Fig. 9. . Interface of the software. AMI dynamics of drying drops of saliva taken from viral hepatitis B patients (black) and healthy donors (white). X-axis is time (min), Y-axis is AMI in calculated units.

METHOD AND APPARATUS FOR DETERMINATION OF MEDICAL DIAGNOSTICS UTILIZING BIOLOGICAL FLUIDS

RELATED APPLICATIONS

The present invention is a continuation in part of Ser. No. 10/466,845 filed on Jul. 21, 2003 and now U.S. Pat. No. 6,874,357, and incorporated by reference herein as if fully rewritten.

BACKGROUND OF THE INVENTION

1. Field of the Invention

The present invention relates generally to a method of medical diagnostics of fluids, and, more particularly, to an apparatus for carrying out such methods utilizing the acousticomechanical impedance (AMI) characteristics associated with the properties of drying droplets of biological fluids.

2. Description of the Related Art

A sessile drop is a specific physical object. The initial shape of a drop is a function of its physical properties and substrate nature. In the same environment the following factors play a significant role in the dynamics of the drop drying process: surface tension, wettability, viscosity, inner structure, dispersion of colloids, heat conductance, ionic force, gel-forming substances, and cover skin density. Even the slightest variation in the composition of a liquid leads to the total change in these parameters during drop drying.

In recent years the effect of a drying drop as a natural model of self-organizing system with an extensive set of process variations has become a subject of an increasingly active research interest worldwide. The diagnostics in this research relied on the morphological structures seen with a microscope in dried droplets of biological liquids, and on their verbal description. One approach provides diagnostic information drawn all through a droplet drying process as described in U.S. Pat. No. 6,874,357, issued in the name of Yakhno et al and incorporated by reference herein as if fully rewritten. The use of a subjective characterization of a drying drop of multicomponent fluid is described. The present invention is devoted to the medical applications utilizing these previous teachings.

In medicine, bodily fluids are often subjected to analysis where the levels of proteins, macromolecules and other natural constituents of bodily fluids are measured. The absence or presence of pathogens is often examined as well. These analyses often measure the level of formation of a colored product. Alternatively, specific antibodies against proteins or pathogens can be utilized. A unique kit of reagents is necessary for each such test, and often a separate machine is used for only a limited number of laboratory tests. This greatly increases the expense of body fluid analysis.

Of particular interests is blood serum, but other biological liquids are anticipated as useful, including urine and saliva. A dried droplet of serum from a healthy person is a central-symmetry figure and resembles a rosette owing to a slightly concave shape and regular arch-like cracks. The peripheral zone is mostly protein and in the center there are salt structures. This symmetry is disturbed in a diseased person, the structuring character changes, and dried drops take atypical forms. It has been established that there is a relation between the nosology of a disease and the qualitative changes in a drop shape, which is used as an additional criterion in medical diagnostics. The central zone in dried drops of different biological liquids from the same person is of the same morphological type. The character of the central zone structuring in dried drops depends on their viscosity: liquids with a lower viscosity factor form well organized clear-interface structures.

Diagnostic assays using saliva are a relatively new but growing technology. The FDA approved the first HIV test based on saliva rather than blood. Besides, a new technology is being actively developed currently, the HIV Urine Test, which was also approved by the FDA.

The need exists for a method in which a plurality of analyses of the contents of body fluid could be performed using one device or machine. In the manufacturing and storage of materials, such as fossil fuels, and pharmaceuticals, quality control must be assured, to ascertain that the materials manufactured have not deteriorated in the course of manufacture or with the passage of time. Chromatography is often utilized, and the specific reaction conditions for each material undergoing analysis must be found. The need exists for a simple method in which little calibration need be performed before analysis of highly dissimilar materials.

Consequently, a need has been felt for providing an apparatus and method based on two phenomena: nonlinear dynamic processes in drying drops of biological fluids; and, a possibility of utilizing these processes by means of a diagnostic method, test or device developed for this task.

SUMMARY OF THE INVENTION

A feature of the present invention that is a radical difference from known prior art is that what is used as the informative parameter is the temporal dependence of the acoustical-mechanical impedance (AMI) of the drying drop as a unit.

Briefly described according to a preferred embodiment of the present invention, a drop of biological fluid of volume 5 microliters is dried on the surface of a quartz resonator oscillating with constant ultrasound frequency. This frequency is selected to agree with the resonance frequency of the unstrained resonator. The shear characteristics of the drop, which are extremely sensitive to the occurrence and increase in the new-phase structures on the surface between the drop and the quartz plate, are observed. The measured quantity is the dynamical complex conductance of the resonator, which is converted to the acoustical-mechanical impedance (AMI) of the drying drop, and the drying dynamics is displayed in the form of a curve. The dynamical characteristics of integral mechanical properties of drying droplets of blood serum, urine, and saliva were studied by measuring the acoustic-mechanical impedance (AMI) using a computer-controlled equipment described earlier. When the liquid drop sample is drying on the surface of a quartz resonator plate oscillating at a constant frequency (equal to the resonance frequency of an unloaded resonator, 60 kHz), there arises a shear wave highly sensitive to the formation and growth of a new phase at the liquid-quartz interface. The current invention measures a change in the complex electric conductivity of the liquid-quartz system, calculates the parameters of the AMI dynamics in the drying drop, and displays their variation on the monitor at the real time scale in the form of a curve. At a time the optical properties of drying drops were observed. For each disease or a physiological state the geometrical features of the curves were extracted and then the shape indices were calculated.

In accordance with the teachings of the present invention, each "pathology" group differed from the "norm" by its specific shape index.

Further, the present invention provides the capability of identifying the formation of the morphological and dynamical differences in drying drops of biological liquids of healthy and sick.

It is the object of the present invention to provide a method for the analysis of fluids, useful for diagnostics of a wide variety of materials in liquid from, and for many constituents of a fluid. In this method, a single device can be utilized to analyze highly dissimilar fluids, such as bodily fluids, fossil fuels, and pharmaceuticals. The method hereby disclosed utilizes a simple device, which does not need be calibrated specifically for each type of material, thereby shortening the length of the analysis and simplifying the analysis. These and other objects of the present invention will become more apparent from the summary of the invention and the detailed description of the preferred embodiments, that follows. The method of the present invention can be applied to any material in fluid form, and the scope of the invention is not limited to bodily fluids, pharmaceuticals or fossil fuels.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 1 illustrates a drop of fluid undergoing analysis, and its placement on a quart crystal connected to a resonator.

FIG. 2 illustrates a wave emitted from the resonator, and the direction of passage of the wave through the drop of fluid.

FIG. 3 is a graph summarizing the AMI profiles of plasma samples taken from a group of pregnant females with normal deliveries, versus AMI profiles of a group of females with pre-term deliveries and versus those of a group of non-pregnant females, as in Example 1

FIG. 4 is a graph correlating the AMI plasma values measured for normal deliveries in Example 1, with the week of pregnancy during which the sample was taken FIG. 5 is a graph correlating the AMI plasma values measured for pre-term deliveries in Example 1, with the week of pregnancy during which the sample was taken.

FIG. 6 illustrates two saliva samples undergoing analysis, and the AMI profiles generated from them in Example 2.

FIG. 7 illustrates the AMI profiles of two types of petrol, analyzed in Example 3

FIG. 8 illustrates the AMI profiles of three types of alcohol, analyzed in Example 4.

FIG. 9 illustrates the AMI profile of a saliva sample taken from a healthy individual versus that of a Hepatitis B patient, as described in Example 5.

DESCRIPTION OF THE PREFERRED EMBODIMENTS

The best mode for carrying out the invention is presented in terms of its preferred embodiment, herein depicted in conjunction with the Figures.

Detailed Description of the Figures

It is appreciated that the detailed description that follows is intended only to illustrate certain preferred embodiments of the present invention. It is in no way intended to limit the scope of the invention, as set out in the claims.

The present invention discloses a method for measuring changes in the composition of a fluid, wherein a vibrating wave released from a quartz resonator is directed into a drop of fluid undergoing analysis. The rate of movement of the wave within the drop of fluid depends on the viscosity, composition, surface tension, and adhesion of the fluid, and the temporary arrangement of molecules inside the drop. These values are reflected in the "acoustic-mechanical impedance" (AMI) of the fluid, which is calculated for the fluid undergoing analysis, based on the change in the electrical voltage amplitude of the crystal, as measured over time. Every fluid has a different set of AMI values as measured over time, during partial drying of the drop.

The AMI "profile" (a set of AMI values measured over time) depends on the components of the fluid, and the previously mentioned values of viscosity, surface tension, etc. Thus the AMI profile of each fluid undergoing analysis is compared to the AMI profile of an appropriate control fluid. For instance, when blood serum is analyzed to determine the presence of a protein which indicates disease, the AMI profile is compared to that of the serum of a healthy individual. Alternatively, when the method is used for quality assurance, the AMI profile of a material stored over a period of time, is compared to the AMI profile of newly manufactured material. Referring to FIG. 1, in the method disclosed hereby, a drop of fluid(1) is placed in direct contact with a quartz crystal(2). The crystal is connected via wires (3) to an electrical circuit which includes a resonator connected to the quartz crystal, and the circuit emits a sinusoidal voltage wave at a set frequency, of, for example, 60 kHz.

The wave (having a fixed frequency) is connected to a bridge circuit. Referring to FIG. 2, the resonator is activated, and a shear wave of ultrasound(4) is released from the crystal to enter the drop of fluid(1). The voltage output of the bridge circuit is measured and sampled over a predetermined period of time, such as 1-40 minutes. The voltage output is dependant upon the nature of the fluid. The AMI values are calculated (see below) and are plotted as a function of time, and compared to the AMI values of a relevant control fluid, previously measured, or to previously accumulated data charts. The comparison reveals the state of the fluid, and detects changes in the fluid as compared to the control fluid. The bridge circuit is designed to offset the internal capacity of the resonator, and the influences of external capacities, such as that of the connecting wires. The bridge circuit is adjusted after the drop is placed upon it so that the voltage output is at first set to be zero, and then changes in the voltage that occur over time are measured. Alternatively, the voltage can be calibrated to be zero before the drop is placed upon the crystal, and changes in the voltage are measured from the first moment that the drop is placed upon the crystal.

Parameters of the measuring circuit are chosen to provide the input signal U of the device $$U \approx |Z|^2 \qquad 1.$$

where |Z| is the AMI modulus of the object contacting the resonator surface.

As long as the drop is liquid, the induced impedance is proportional to the characteristic resistance of the viscous wave:

$$|Z| \approx S(f\eta\rho)^{1/2}, \qquad 2.$$

where "S" is the area of contact between the drop and the resonator surface; "$\eta$" is the viscosity of the liquid $\rho$ is its density; and "f" is the frequency of resonator oscillations. For the liquids tested below in the Examples section, $\eta \approx 10-2$ Pa·s and $\rho \approx 10^3$ kg/m³. Under those conditions the depth of penetration of a viscous wave was of an order of 10 mcm and the recorded output signal corresponded to $$U \sim S^2 \eta \rho \qquad 3.$$

According to Equation (3), the magnitude of the signal is highly sensitive to the area of the drop, which, in turn, depends on the magnitude of surface tension and moistening. In addition, dynamics of phase transitions depends on the geometry (bell shape) that is also determined by the magnitude of surface tension and moistening.

As the drop dries, the induced AMI changes both quantitatively and qualitatively. Nevertheless, the relationship described in Equation (1) between the output signal and induced impedance modulus holds true.

The proposed method enables does not require use of reagents and can be performed by medium-level science personnel in clinical and scientific laboratories.

There is thus provided in the present invention, a method for measuring changes in the composition of a fluid, useful for medical diagnostics or quality control of fluids, comprising:

One) placing a drop of fluid upon a predetermined area of a quartz crystal;

Two) generating ultrasonic vibrations of a predetermined frequency in said crystal; wherein the vibrating wave is directed into the drop of fluid in a vertical direction relative to the area of said crystal upon which the drop is placed;

Three) measuring voltage changes over a bridge circuit connected to the crystal, over a time period during which total or partial evaporation of the liquid occurs;

Four) comparing the results of said measurements to previously obtained results or to predetermined data;

Five) detecting changes in the composition of the fluid, from said results.

In accordance with a preferred embodiment of the present invention, the fluid is a bodily fluid. In certain embodiments, the bodily fluid is selected from blood, a blood component, saliva, sputum, urine, feces, semen, or sweat. Various specific examples are herein shown and discussed.

EXAMPLE 1

The inventors wished to determine if there was a measurable difference in the blood plasma of mothers who gave birth to live babies born at term, versus mothers who gave birth prematurely. This is of import if the plasma of the mother contains information about the state of fetal development, and thus a prediction of impeding premature birth could be made and corrected for. Mother and fetus have individual blood circulation systems, and thus it is not obvious that fetal markers would be present in the mother's plasma.

Plasma specimens were obtained from age-matched non-pregnant and pregnant females.

Specimens were obtained from pregnant women at various gestation times and later assigned to "normal" or "problematic" pregnancy groups according the ultimate result of the pregnancy. Problematic pregnancies were those that resulted in a pre-term delivery, or in other complications, such as underdeveloped lungs, and low birth weight. All specimens were tested on the day of sampling (fresh, not-frozen, plasma). 5 μl of plasma were applied to the horizontal flat surface of an electro-acoustic quartz resonator switched to a measuring circuit and oscillating at a frequency of 60 kHz, with a shear wave excited in the drop. The measuring circuit recorded the resonator response to the acoustic-mechanical impedance introduced by the sample and its dynamics in given intervals of time (0.1 min) until free solvent was completely evaporated.

For these results, and for the following examples (1-5):

$$|Z| \approx S(f \eta \rho)^{1/2} \qquad (2)$$

where "S" is the area of contact between the drop and the resonator surface; "$\eta$" is the viscosity of the liquid p is its density; and "f" is the frequency of resonator oscillations. For Examples 1-5, $\eta \approx 10-2$ Pa·s and $\rho \approx 103$ kg/m$^3$. Under these conditions the depth of penetration of a viscous wave was of an order of 10 mcm and the recorded output signal corresponded to U $\sim$S2$\eta \rho$ Referring to Table 1, AMI results are presented for 15 non-pregnant women. In Table 1, and in the following Tables 2-3, samples were identified by both a sample number (1-15), and by the initials of the patient (when the latter were available).

TABLE 1

AMI Plasma Values Of Non-Pregnant Women

| Patient # | Initials | AMI-Plasma Value |
|---|---|---|
| 1 | V.N.V. | 6.4 |
| 2 | *** | 7.7 |
| 3 | *** | 5.1 |
| 4 | S.O.I. | 6.3 |
| 5 | *** | 9.2 |
| 6 | *** | 7.9 |
| 7 | *** | 6.9 |
| 8 | G.O.V. | 5.7 |
| 9 | *** | 4.3 |
| 10 | *** | 7.4 |
| 11 | B.I.V. | 7.1 |
| 12 | *** | 8.4 |
| 13 | *** | 6.8 |
| 14 | *** | 10.0 |
| 15 | I.Y.I. | 7.4 |

Referring to Table 2, AMI results are presented for normal deliveries.

TABLE 2

AMI Plasma values of women with normal deliveries

| Patient # | Initials | AMI-Plasma Value |
|---|---|---|
|  | D.I.P. | 14.4 |
|  | O.I.G. | 11.9 |
|  | Z.F.S. | 11.1 |
|  | *** | 10.5 |
|  | *** | 12.2 |
|  | B.M.N. | 16.5 |
|  | N.A.A. | 15.3 |
|  | S.E.M. | 17.4 |
|  | D.O.P. | 14.3 |
| 1 | O.N.A. | 14.0 |
| 1 | M.O.A. | 18.3 |
| 1 | O.E.B. | 13.9 |
| 1 | M.M.C. | 14.7 |
| 1 | K.E.A. | 10.1 |
| 1 | B.L.V. | 15.2 |
| 1 | D.A.A. | 13.7 |
| 1 | T.A.A. | 16.8 |
| 1 | B.O.B. | 13.8 |
| 1 | N.L.V. | 14.9 |
| 2 | *** | 14.9 |
| 2 | S.I.V. | 7.2 |
| 2 | K.O.B. | 12.2 |
| 2 | M.N.E. | 10.0 |
| 2 | E.N.V. | 7.0 |
| 2 | M.N.D. | 8.6 |
| 2 | T.L.Yu | 12.2 |
| 2 | *** | 10.5 |

TABLE 2-continued

AMI Plasma values of women with normal deliveries

| Patient # | Initials | AMI-Plasma Value |
|---|---|---|
| 2 | *** | 15.0 |
| 2 | *** | 15.2 |
| 3 | *** | 14.6 |

*** Initials are not available.
Mean Value 13.2, SD ± 2.9

Referring to Table 3, AMI results are presented for pre-term deliveries

TABLE 3

AMI plasma values of women with pre-term deliveries

| Patient # | Initials | AMI-Plasma Value |
|---|---|---|
| 1 | T.N.A. | 8.8 |
| 2 | *** | 8.7 |
| 3 | *** | 4.9 |
| 4 | *** | 8.2 |
| 5 | M.S.Yu | 9.0 |
| 6 | *** | 7.1 |
| 7 | *** | 6.8 |
| 8 | *** | 7.2 |
| 9 | B.E.V. | 6.8 |
| 10 | S.L.V. | 10.7 |
| 11 | *** | 8.7 |
| 12 | *** | 9.1 |
| 13 | B.O.A. | 7.4 |
| 14 | *** | 8.5 |
| 15 | *** | 7.6 |
| 16 | R.A.I. | 6.4 |
| 17 | *** | 8.2 |
| 18 | *** | 8.1 |
| 19 | *** | 9.5 |
| 20 | *** | 11.4 |
| 21 | C.S.V. | 10.0 |
| 22 | *** | 6.5 |
| 23 | C.C.A. | 7.2 |
| 24 | *** | 10.6 |
| 25 | A.E.G. | 5.8 |
| 26 | *** | 4.9 |
| 27 | *** | 6.2 |
| 28 | F.S.V. | 8.1 |
| 29 | *** | 9.0 |
| 30 | *** | 11.2 |

*** Initials are not available.
Mean Value 8.1, SD ± 1.4

Results of the research demonstrated a marked difference in the AMI values of the plasma taken from the different groups of women, which is summarized in FIG. 3, prepared after statistical analysis was performed for each group. Referring to FIG. 3, the AMI level is significantly elevated in the maternal plasma of normal deliveries (denoted on the graph as "Norm. D.", column 2) as compared to the AMI level in non-pregnant females (denoted as "Non.Pr.", column 1). In contrast, there was no change in the AMI levels in problematic pregnancy (denoted "Pre-term D", column 3) as compared to non-pregnant control females.

Referring to FIG. 4, a graph is depicted correlating the AMI plasma values measured for normal deliveries, with the week of pregnancy during which the sample was taken. It is important to note that AMI levels in normal pregnancies are significantly elevated as early as the 6th week of gestation, and stay almost constant until delivery.

Referring to FIG. 5, a graph is depicted, correlating the AMI plasma values measured for pre-term deliveries, with the week of pregnancy during which the sample was taken. AMI levels in abnormal pregnancies are typically lower than those of normal pregnancies, as early as the 6th week of gestation.

It appears therefore that the method disclosed in the present invention has the potential to predict the outcome of pregnancy as soon as pregnancy is verified or very soon thereafter. If this observation is validated in further clinical studies, the method of the present invention far exceeds the capability of the currently existing in vitro tests for the prediction of premature and abnormal deliveries as early as the 6th week of gestation. Beyond its diagnostic value, this technology can serve as a pivot for research into the causes of pregnancy problems and for the development of preventive or therapeutic means. It is evident that this method can provide a direct monitoring tool to be used in conjunction with other medical treatment currently available.

EXAMPLE 2

A drop of saliva was taken from two donors and placed on the quartz resonator as in Example 1. The voltage output of the bridge circuit was measured as the drops dried and the liquid evaporated.

Referring to FIG. 6, the ratio of albumin (outer ring) and saline (central ring) constituents is different in the saliva taken from the different donors. This can be visualized in the photographs, and can be seen as plotted in the AMI profile curves shown in the lower half of FIG. 6. Thus, the method described here can be used to distinguish between two similar samples of bodily fluid. This is useful in the field of medical diagnostics.

EXAMPLE 3

Two types of petrol were subjected to analysis as in Example 1. Referring to FIG. 7, petrol type 1, A96, is termed "series 1", and petrol type 2, A 76, is termed "series 2". Results show that the method of the present invention can readily differentiate between the two, based on their AMI profiles.

EXAMPLE 4

Three alcohols were subjected to analysis as in Example 1. Referring to FIG. 8, No. 1=methanol, No. 2=ethanol, No. 3=mixture of ethanol and methanol 1:1. The three types of alcohol are readily distinguishable, based on their distinct AMI profiles.

EXAMPLE 5

A saliva sample was taken from two donors; one healthy, and one a patient ill with hepatitis B. Samples were subjected to analysis as in Example 1. Referring to FIG. 9, AMI profile number 1 relates to the hepatitis B victim, while AMI profile number 2 relates to the healthy individual. The method disclosed in the present invention can readily distinguish between the two profiles, thus this method can be used to diagnose the presence of hepatitis B virus.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents. Therefore, the scope of the invention is to be limited only by the following claims.

What is claimed is:

1. A method for measuring changes in the composition of a fluid, useful for medical diagnostics or quality control of fluids, comprising the steps
   a. placing a drop of fluid upon a predetermined area of a quartz crystal;
   b. generating ultrasonic vibrations of a predetermined frequency in said crystal;
   wherein the vibrating wave is directed into the drop of fluid in a vertical direction relative to the area of said crystal upon which the drop is placed;
   c. measuring voltage changes over a bridge circuit connected to the crystal, over a time period during which total or partial evaporation of the liquid occurs;
   d. comparing the results of said measurements to previously obtained results or to predetermined data; and
   e. detecting changes in the composition of said fluid, from said results.

2. The method according to claim 1, wherein said fluid is a bodily fluid.

3. The method according to claim 2, wherein said bodily fluid is selected from blood, a blood component, saliva, sputum, urine, feces, semen, or sweat.

4. The method according to claim 1, wherein said fluid is a fossil fuel.

5. The method according to claim 1, wherein said is an alcohol.

6. The method according to claim 1, wherein the said drop of said fluid has a volume of 5 microliters.

7. A method for measuring changes in the composition of a fluid, useful for medical diagnostics or quality control of fluids, said method comprising the steps:
   a. Selecting an electro-acoustic resonator having a first side opposite a second side along a longitudinal axis;
   b. Placing a drop of multi-component fluid on said first side;
   c. Imparting an oscillation on said resonator along said longitudinal axis at said second side; and
   d. Measuring the changes caused in the acoustical mechanical impedance caused to said resonator as said drop dries.

8. The method of claim 7, wherein said imparted oscillation is a shear oscillation imparted at a constant frequency.

9. The method of claim 8, wherein said imparted oscillation is of a sinusoidal form.

10. The method of claim 9, wherein said imparted oscillation corresponds to a frequency of the first longitudinal resonance of said resonator.

11. The method of claim 7, wherein said resonator comprises a rectangular plate of quartz.

12. The method of claim 7, wherein said measuring comprises:
   a. Applying an electric field to said resonator in a direction perpendicular to said imparted oscillation;
   b. Tracking the electric conductance of said resonator as said drop dries;
   c. Generating an amplitude curve from said tracking that corresponds to the modulus of the acoustic-mechanical impedance of said resonator-drop combination;
   d. Mapping said amplitude curve; and
   e. Analyzing the particular geometry of said amplitude curve.

13. The method of claim 12, wherein said analyzing of said particular geometry of said amplitude curve includes comparing said mapped amplitude curve against a known amplitude curve.

14. The method of claim 12, wherein said analyzing of the particular geometry of said amplitude.

15. The method of claim 14, wherein said spatio-temporal development and phase transitions is used for integral estimation of medical diagnostics and biological fluid quality.

16. The method of claim 14, wherein the dynamics of said acoustal-mechanical impedance of the drying drops that reflects the variation in their viscoelastic properties is used as an identifying characteristic of a biological liquid.

17. The method of claim 7, wherein said resonator comprises:
   a rectangular plate of quartz capable of receiving a drop of biological fluid at one end;
   a plurality of electrical conductors affixed tot he center of said rectangular plate and in electrical communication with an excitation voltage;
   means for imparting longitudinal mechanical oscillation to said rectangular plate; and
   means for measuring the changes in the excitation voltage; wherein changes in the excitation voltage caused by the drying of said drop on said plate corresponds to said acoustal-mechanical impedance of said plate-drop combination.

* * * * *